Figure 1:
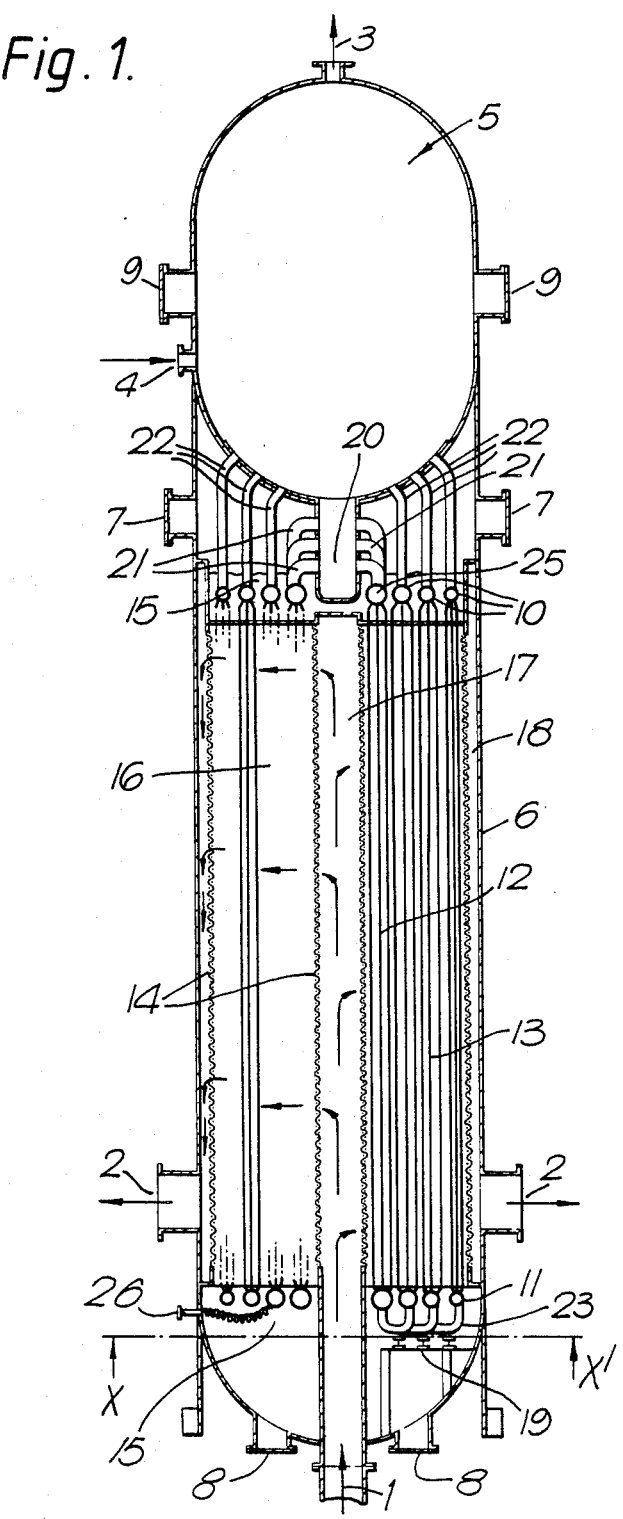

United States Patent [19]
Dobson et al.

[11] Patent Number: 4,882,444
[45] Date of Patent: Nov. 21, 1989

[54] CHEMICAL REACTOR AND PROCESS

[75] Inventors: Brian Dobson; Peter J. M. Whyman, both of Cleveland; Ralph J. Doy, Saltburn-by-the-Sea; Manfred O. Engel; Raymond Davies, both of Cleveland, all of England

[73] Assignee: Imperial Chemical Industries PLC, London, England

[21] Appl. No.: 764,973

[22] Filed: Aug. 12, 1985

Related U.S. Application Data

[63] Continuation of Ser. No. 447,942, Dec. 8, 1982, abandoned.

[30] Foreign Application Priority Data

Dec. 14, 1981 [GB] United Kingdom ............... 8137683

[51] Int. Cl.⁴ ........................................ C07D 301/10
[52] U.S. Cl. ................................................. 549/534
[58] Field of Search ........................................ 549/534

[56] References Cited

U.S. PATENT DOCUMENTS 2,744,813  5/1956  Paul ..................................... 422/208

FOREIGN PATENT DOCUMENTS 719562   4/1942  Fed. Rep. of Germany .
2046618 11/1980  United Kingdom .

Primary Examiner—Richard L. Raymond
Assistant Examiner—Mark W. Russell
Attorney, Agent, or Firm—Cushman, Darby & Cushman

[57] ABSTRACT

In an exothermic reaction the reactants are passed through a fixed catalyst bed through which heat exchange tubes pass, reactants are flowed transversely to the tubes, heated by a first group of tubes and cooled by a second group of tubes, heat exchange fluid being passed from the first group of tubes to the second. This reduces the need to preheat incoming reactants.

7 Claims, 2 Drawing Sheets

CHEMICAL REACTOR AND PROCESS

This is a continuation of application Ser. No. 447,942, now abandoned filed Dec. 8, 1982.

This invention relates to a chemical reactor and process.

Chemical reactors in which horizontal flow of the reactants takes place are known and reactors have been proposed in which reactants are flowed radially through an annular catalyst bed. In UK Patent Application No. 2,046,618 a reactor of this type is proposed in which heat exchange fluid tubes are disposed vertically in the catalyst bed to remove heat generated by reaction in the catalyst bed. The reactants are pre-heated to reaction temperature before being passes into the reactor.

It is an object of this invention to reduce the need to pre-heated reactants which are passed into a catalyst bed. To this end heat exchange tubes disposed in the catalyst bed are used to heat incoming gases when they meet the catalyst bed using heat derived from the heat of reaction in other parts of the catalyst bed.

This invention comprises a process for carrying out an exothermic chemical reaction which comprises passing reactants through a fixed catalyst bed in which the reactants are passed transversely past heat exchange tubes which pass through the bed in which in a first part of the bed the reactants are heated by contact with a first group of heat exchange tubes and in a second part of the bed they are cooled by contact with a second group of heat exchange tubes, heat exchange fluid from the first group of tubes being passed to the second group of tubes.

The invention also comprises a chemical reactor for carrying out the process of the invention which comprises means for holding a catalyst bed, a reservoir above the catalyst bed for a heat exchange fluid which is vapourizable under the operating temperatures and pressures of the reactor, heat exchange tubes extending into the region to be occupied by the catalyst bed which are connected to the heat exchange fluid reservoir, and means for passing reactants through the catalyst bed transversely to the tubes, the tubes being so connected and oriented that when an exothermic reaction is carried out in the catalyst bed the heat exchange fluid passes through them by thermosyphon action in a sense such that the downcomers are disposed in the region of intake of the reactants to the catalyst bed and risers are disposed in other regions of the catalyst bed.

Suitably the heat exchange tubes are upright; for example they may be vertical as this optimizes the thermosyphon action. By thermosyphon action we mean a motion of fluid in a circuit in which vapourisation of the fluid in the return part of the circuit provides a motive force maintaining the circulation.

It is preferred that flow in the reactor should be radial; that is the catalyst bed should be annular and that reactants should be fed radially through it by feeding the reactant either to an outer envelope surrounding the annular catalyst bed to an inner core space through which they are withdrawn or preferably by feeding the reactants to a central core space and withdrawing products from an envelope surrounding the annular catalyst bed. The bed is suitably bounded by porous barriers through which the gas passes and the outer envelope is suitably defined outwardly by an impermeable reactor shell.

In order to optimise a thermosyphon action in the desired direction the downcomers are preferably bed with liquid heat exchange fluid from a low position in the reservoir at which the liquid is substantially free from vapour. In passing down the downcomers, vaporisation does not occur because the tube is losing rather than gaining heat and the head of pressure on the fluid increases as it passes downwards. On completing the circuit by passing up a riser vaporisation occurs because heat is received from the catalyst bed at this position and the pressure is reduced as the fluid rises. Because of the vaporisation of heat exchange fluid in the riser the density of heat exchange fluid in the riser is less than that in the downcomer and this provides a driving force maintaining circulation. The riser is suitably discharged into a higher part of the reservoir than that at which the downcomers are fed. The system can however work even if risers and downcomers are connected to a heat exchange fluid reservoir at the same level or if the risers are connected at a lower level than the downcomers because the thermal effects suffice to maintain circulation.

The heat exchange fluid reservoir may if desired be divided into compartments for the receipt of fluid from the risers and for feeding fluid to the downcomers and may be designed in any way necessary to allow disengagement of vapour from liquid. In a preferred construction the heat exchange fluid reservoir is integral with a reactor shell housing the entire reactor. Such an arrangement is both simple and effective and allows a robust construction of the reactor.

Tubes connected to the reservoir need be supported only from the top, and it is preferred that this should be done as if they are supported at other points also thermal expansion of the tubes requires the movement of the latter supports relative to the shell. This may be achieved by the use of flexible bellows for pipework supporting the tubes or by the use of a convoluted reactor shell, which will allow supports borne by the shell to move with the relevant part of the shell, but such complication is better avoided for reasons both of safety and of cost.

Reactors of this invention are very suitable for carrying out strongly exothermic processes, for example the oxidation of ethylene to ethylene oxide by contacting ethylene with oxygen in the presence of a catalyst which is normally a supported silver catalyst the support usually being $\alpha$-alumina. The catalyst may be promoted with an alkali and/or alkaline earth metal and the reaction may be moderated by feeding a gaseous chlorine containing reaction moderator, for example ethylene dichloride or vinyl chloride to the reaction. The process is normally carried out at an elevated pressure, for example 5 to 50 atmospheres and at a temperature in the range 200° to 300° C. In the reaction, part of the ethylene is oxidised to carbon dioxide and water, which reaction is highly exothermic.

Figure 2:
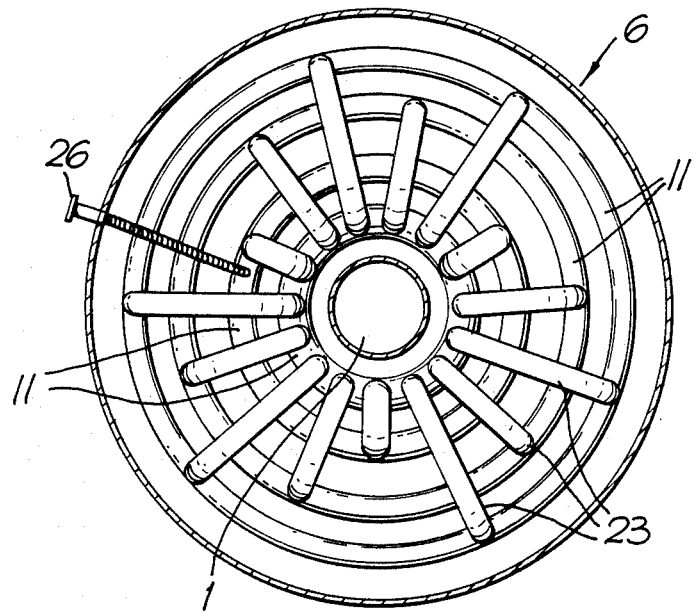

One form of reactor according to the invention will now be described with reference to the drawings of which FIG. 1 shows a cross-section through the axis of the reactor and FIG. 2 shows a view upwards from X-X'.

The reactor comprises a reservoir 5 which is integral with reactor shell 6, the axis of the shell and reservoir being vertical. Downcomers 21 leading from reservoir sump 20 feed a ring header 25 from which downcomers 12 pass through catalyst bed 16 to a bottom ring header 11. Bottom ring header 11 is connected as shown in FIG. 2 to three other concentric ring headers of increasing diameter via redistributors 23. From the outer three ring headers, rises 13 pass through catalyst bed 16 to top ring headers 10 and which are connected via risers 22 to reservoir 5.

The catalyst bed is of annular form and is bounded by catalyst containment mesh 14 on its inner and outer faces. Feed inlet 1 feeds gases to the axial compartment defined thereby and product gas exit 2 removes product from the annular space 18 surrounding the outer face of the catalyst bed and defined by the catalyst containment mesh and the shell of the reactor 6. Manways 7 are provided for loading catalyst into the bed and manways 8 are provided for removing catalyst from the bed. Inlet 4 is provided for introducing water or other heat exchange fluid into the reservoir and exit 3 is provided for vapour. Inspection manways 9 are provided for inspection of the reservoir 5. If desired inert packing 15 may be provided at the top and bottom of the catalyst bed. Supports 19 are suitably provided during construction of the reactor but are preferably removed when construction is complete.

The reactor may be operated as follows. Inert packing, catalyst and an upper layer of inert packing may be introduced through manways 7. A heat exchange fluid at an appropriate temperature and pressure is introduced through inlet 4. This drains into the sump 20 through downcomers 12 through redistributors 23 and through risers 13 until the tube system is filled with it. The gas mixture to be reacted is passed into the axial (core) compartment and passes through the catalyst bed to the annular compartment 18 from which it is removed. Heat generated by reaction causes boiling in the risers. Because of this the density of the material in the risers will be less than that in the downcomers and fluid will flow down the downcomers and up through the risers. In steady state operation therefore fluid will pass from the sump through the downcomers thus heating the inlet gases when they enter the catalyst bed and will pass up the reservoirs conducting heat away from the other portions of the catalyst bed by thermosyphon action. On entering reservoir 5 the mixture of liquid and vapour from the reservoirs disengages, the liquid passing to the sump 20 and the vapour passing from outlet 3.

During start-up and shutdown of the reactor, the temperature is controlled by external heating or cooling of the heat exchange fluid. In order to create a flow of heat exchange fluid through the tubes during start up vapour may be passed into one or more of the bottom ring headers 11 through a coiled vapour injector pipe 26. When reaction commences the thermosyphon effect is self sustaining and no further vapour need be injected through pipe 26.

We claim:

1. A process for carrying out an exothermic chemical reaction between gaseous reactants in a fixed catalyst bed through which the reactants flow in a flow direction whereby the entering reactants are in a cooler portion of the bed relative to a hotter portion where the exothermic reaction occurs, said process comprising: heating the cooler portion of the bed with a heated heat exchange fluid passed through a first group of heat exchanger tubes extending through the cooler portion of the bed in a direction transverse to said flow direction; then passing the heat exchange fluid from said first group of heat exchanger tubes to a second group of heat exchanger tubes extending through the hotter portion of the bed in a direction transverse to said flow direction to cool said hotter portion and to heat the heat exchange fluid, thereby providing said heated heat exchange fluid which is passed through said first group of tubes.

2. A process as in claim 1 wherein said fixed catalyst bed is annular and has a vertical axis and a central core space and wherein said flow direction is radially through said bed.

3. A process as in claim 2 wherein said flow direction is radially outward through said bed whereby said cooler portion of said bed wherein said first group of heat exchanger tubes is located is the innermost portion of said bed and whereby said hotter portion of said bed wherein said second group of heat exchanger tubes is located radially outwardly of said innermost portion.

4. A process as in claim 3 wherein said annular catalyst bed has a vertical axis, wherein said heat exchange tubes are vertical and wherein the heat exchange fluid passes downward through said first group of heat exchange tubes and upward through said second set of heat exchange tubes.

5. A process as in claim 4 for producing ethylene oxide wherein said reactants are ethylene and oxygen and wherein said catalyst bed is a silver catalyst bed.

6. A process as in claim 1 wherein said flow direction is substantially horizontal, wherein said heat exchanger tubes are substantially vertical, wherein the heat exchange fluid is in liquid form in said first group of heat exchange tubes and flows downwardly therethrough and wherein said heat exchange fluid is vaporized in said second group of heat exchanger tubes and flows upwardly therethrough thereby creating thermosyphon flow.

7. A process as in claim 6 for producing ethylene oxide wherein the gaseous reactants are ethylene and oxygen.

* * * * *